United States Patent
Bak et al.

(10) Patent No.: US 6,365,801 B1
(45) Date of Patent: Apr. 2, 2002

(54) GUZMANIA PLANT NAMED 'JAZZ'

(75) Inventors: Elly Bak, Rijsenhout; Nicolaas D. M. Steur, Oude Niedorp, both of (NL)

(73) Assignee: Corn. Bak B.V., Assendelft (NL)

( * ) Notice: Subject to any disclaimer, the term of this patent is extended or adjusted under 35 U.S.C. 154(b) by 0 days.

(21) Appl. No.: 09/592,952

(22) Filed: Jun. 13, 2000

Related U.S. Application Data

(63) Continuation-in-part of application No. 09/451,865, filed on Dec. 1, 1999.

(51) Int. Cl.$^7$ .............................. A01H 5/00; A01H 1/00; A01H 1/02
(52) U.S. Cl. .................. 800/298; 800/323; 800/260
(58) Field of Search .................. 800/298, 260, 800/323; Plt./371

(56) References Cited

U.S. PATENT DOCUMENTS

PP10,575 P  *  8/1998  Bak et al. .................. Plt./371

OTHER PUBLICATIONS

Benzing, David H., "The Biology of the BROMELIADS", Mad River Press, Eureka, CA, PP. 1–287(1980).

Rauh et al., "Bromelien Tillandsien und andere kulturwurdige Bromelien", Eugen Ulmer, Stuttgart, Germany, pp. 7–68(1981).

Zimmer et al., "Bromelien Botanik und Anzucht ausgewahlter Arten", Parey, Berlin; Hamburg, Germany, pp. 9–94 (1986).

* cited by examiner

Primary Examiner—Bruce R. Campell
Assistant Examiner—Kent L. Bell
(74) Attorney, Agent, or Firm—Foley & Lardner

(57) ABSTRACT

A Guzmania plant named 'Jazz' particularly characterized by its solid growth habit in a funnel-form rosette measuring approximately 42 cm in height above the pot when flowering; numerous, relatively narrow leaves, each approximately 3–3.5 cm in width and 30–42 cm in length; superior floral bract production; compound inflorescence; floral bracts are bright orange, which especially distinguishes the new cultivar from others, including the cultivar 'Jive'; and long-lasting habit.

5 Claims, 2 Drawing Sheets

(2 of 2 Drawing Sheet(s) Filed in Color)

US 6,365,801 B1

GUZMANIA PLANT NAMED 'JAZZ'

This is a continuation-in-part application of U.S. patent application Ser. No. 09/451,865, filed Dec. 1, 1999, now pending.

FIELD OF INVENTION

The present invention relates to a new and distinct cultivar of Guzmania that is a hybrid, hereinafter referred to by the cultivar name 'Jazz'. The present invention relates to seeds which are Guzmania cultivar 'Jazz', as well as plants and plant parts produced from these seeds which have all the morphological and physiological characteristics of the Guzmania cultivar 'Jazz'. The invention also relates to methods for producing these seeds and plants. Furthermore, the invention relates to progeny plants produced from the cross of 'Jazz' and another Guzmania selection.

BACKGROUND OF THE INVENTION

Guzmania is predominantly epiphytic with a few terrestrial species and is native to the tropics. For the most part, species vary in diameter from 7 or 8 inches to 3 or 4 feet and have rosettes of glossy, smooth-edged leaves.

Floral bracts of Guzmania frequently have brilliant colors and may last for many months. The range of colors for Guzmania is generally from yellow through orange but may also include flame red and red-purple. White or yellow, tubular, three-petalled flowers may also appear on a stem or within the leaf rosette but are usually short-lived.

Guzmania may be advantageously grown as pot plants for greenhouse or home use. Typically, the plants are shaded from direct sunlight. During the spring to autumn period, the central vase-like part of the leaf rosette is normally filled with water.

Guzmania is native to tropical America. Leaves of Guzmania are usually formed as basal rosettes which are stiff and entire and in several vertical ranks. Guzmania plants have terminal spikes or panicles which are often bracted with petals united in a tube about as long as the calyx. The ovary is superior and the seeds plumose.

Asexual propagation of Guzmania is frequently done through the use of tissue culture practices. Propagation can also be from offshoots which can be detached from the mother plant and grown in an appropriate soil or bark mixture.

Methods for cultivation and crossing of Guzmania are well known. For a detailed discussion, reference is made to the following publications, which are incorporated herein by reference: Benzing, David H., *THE BIOLOGY OF THE BROMELIADS*, Mad River Press, Inc., Eureka (1980); Zinuner, Karl, *BROMELIEN*, Verlag Paul Parey, Berlin (1986); and Rauh, Werner, *BROMELIEN*, Verlag Eugen Ulmer, Stuttgart (1981).

A Guzinania inbred is produced by brother/sister crossing over several generations to produce a genetically homozygous plant selection. A hybrid cultivar is produced by crossing two genetically distinct inbred lines, collecting seeds produced by the cross, and germinating seeds so-produced to make hybrid plants. The hybrid seeds and plants produced by this method are uniform with respect to their morphological and physiological characteristics.

A need exists for a greater variety of Guzmania cultivars with attractive ornamental features. Additionally, a need exists for additional Guzrnania hybrid cultivars that can be easily propagated by seed.

SUMMARY OF THE INVENTION

These and other objectives have been achieved in accordance with the present invention which provides a new cultivar 'Jazz' that is a product of a planned breeding program undertaken by the inventors in Assendelft, The Netherlands, in 1994. The male or pollen parent was a selection of *Guzmania lingulata* minor identified by Code No. 94206011. The female or seed parent was a selection of *Guzmania wittmackii* identified by Code No. 94206206.

Both parents have a sufficient degree of homozygosity such that the progeny of the cross are genetically and phenotypically uniform. The variety 'Jazz' therefore can be produced by sexual reproduction by crossing 94206011× 94206206 to produce a population of progeny plants, each of which has the combination of characteristics as herein disclosed for the new cultivar. Seeds produced by crossing 94206011×94206206 have been deposited with the American Type Culture Collection, 10801 University Boulevard, Manassas, Va. 20110-2209, and accorded Deposit Accession No. PTA-3264. 2500 seeds were deposited on Apr. 9, 2001.

The cultivar 'Jazz' can also be produced by asexually reproducing progeny from the cross of 94206011×94206206 because the combination of characteristics as herein disclosed for the new cultivar 'Jazz' are fly fixed and are retained through successive generations of asexual reproduction.

OBJECTS OF THE INVENTION

This invention relates to seeds which produce Guzmania cultivar 'Jazz'.

This invention also relates to Guzmania plants, and parts thereof, having all the physiological and morphological characteristics of Guzmania cultivar 'Jazz'. This invention relates to a plant produced from seeds which are Guzmania cultivar 'Jazz'. This invention also relates to plant parts, such as pollen, seeds or inflorescence produced by Guzmania cultivar 'Jazz'.

This invention relates to a method of producing seeds which are Guzmania cultivar 'Jazz', by crossing *Guzmania wittmackii* selection 94206206 as the female parent with *Guzmania lingulata* minor selection 94206011 as the male parent and the reciprocate cross with 94206206 as the male parent and 94206011 as the female parent and harvesting seeds produced from said crosses.

This invention also relates to a method of producing plants having all the physiological and morphological characteristics of the Guzmania cultivar 'Jazz' comprising the steps of (a) crossing *Guzmania wittmackii* selection 94206206 as the female parent with *Guzmania lingulata* minor selection 94206011 as the male parent; (b) harvesting seeds produced from said cross; and (c) producing plants from said harvested seeds.

Furthermore, this invention relates to progeny Guzmania seeds and plants produced from the cross of 'Jazz', as the male or female parent, with another Guzmania selection.

BRIEF DESCRIPTION OF THE FIGURES

The file of this patent contains at least one drawing executed in color. Copies of this patent with the color drawing(s) will be provided by the Patent and Trademark Office upon request and payment of the necessary fee.

DETAILED DESCRIPTION

Figure 1:
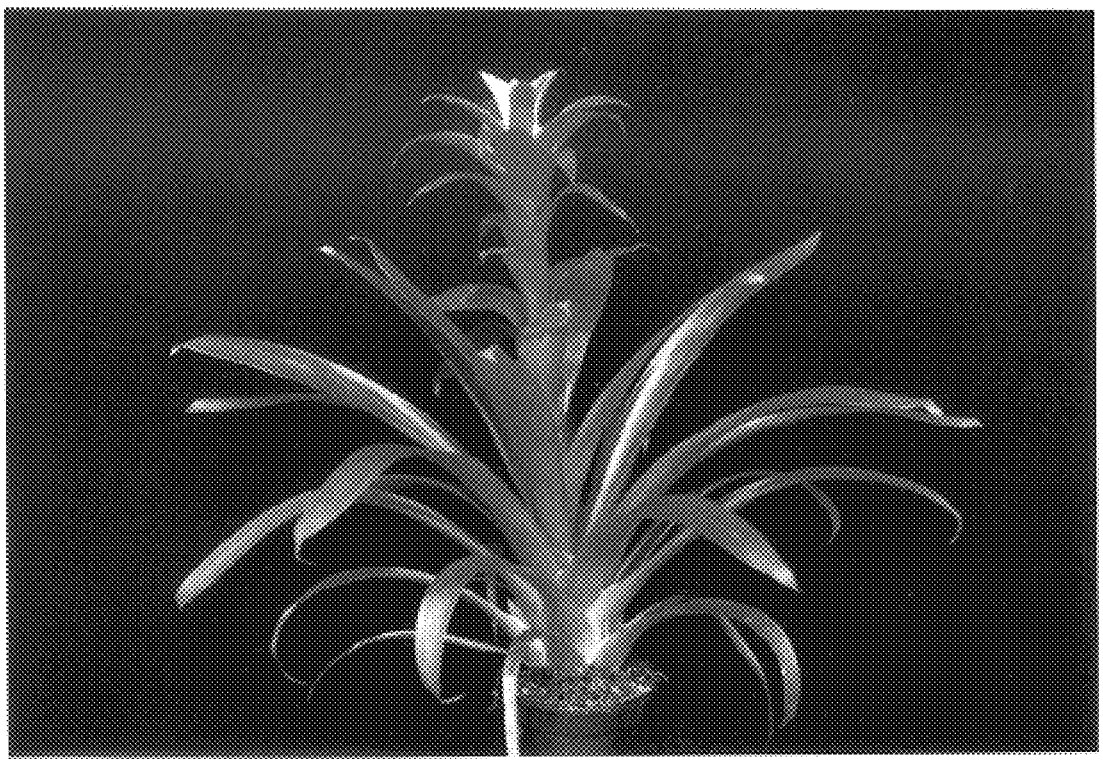
FIG. 1 is a side view of a typical plant of 'Jazz', showing the primary and top bracts, with colors being as true as possible with illustrations of this type.
Figure 2:
FIG. 2 is a close-up view of the inflorescence and top bracts of 'Jazz'.

This invention is directed to a Guzmania plant having all the morphological and physiological characteristics of the cultivar 'Jazz' produced from seeds which are the product of the cross of *Guzinania wittmackii* selection 94206206 as the female parent with *Guzmania lingulata* minor selection 94206011 as the male parent. Both parents have a sufficient degree of homozygosity such that the progeny of the cross were, and continue to be, phenotypically uniform. The variety 'Jazz' therefore can be produced by sexual reproduction by crossing 94206206×94206011 to produce a population of progeny plants each of which has the combination of characteristics as herein disclosed for the new cultivar.

The variety 'Jazz' can also be produced by asexually reproducing progeny from the cross of 94206206×94206011 because the combination of characteristics as herein disclosed for the new cultivar 'Jazz' are firmly fixed and are retained through successive generations of asexual reproduction. The selection comprising the new variety was chosen after commencement of flowering of the progeny in 1997 in Assendelft, The Netherlands. The selection was first asexually propagated through offshoots by, or under the supervision of, the inventors in Assendelft, The Netherlands, with subsequent asexual reproduction being primarily by offshoots. Sexual and asexual propagation has demonstrated that the combination of characteristics as herein disclosed for the new cultivar 'Jazz', as observed in Assendelft, The Netherlands, are firmly fixed and are retained through successive generations of asexual reproduction.

'Jazz' is particularly characterized by the following characteristics:

1. solid growth habit in a funnel-form rosette measuring approximately 42 cm in height above the pot when flowering;
2. numerous, relatively narrow leaves, each approximately 3–3.5 cm in width and 30–42 cm in length;
3. superior floral bract production;
4. compound inflorescence;
5. floral bracts are bright orange, which especially distinguishes the new cultivar from others, including the cultivar 'Jive'; and
6. long-lasting habit.

'Jazz' has not been tested under all available environmental conditions. The phenotype may vary with variations in environmental conditions such as temperature, light intensity, frequency of fertilization, composition of fertilizer, acetylene treatment, day length and humidity without, however, any change in the genotype of the new cultivar.

For example, substantial differences in plant height and diameter, and the number of leaves, can result depending on the size of the plant at the time flowering is induced by acetylene treatment. Since treatment with acetylene to induce flowering disrupts normal watering and fertilization regimens, acetylene treatment of relatively smaller plants adversely affects the growth of the plant.

The following traits have been repeatedly observed and in combination distinguish 'Jazz' as a new and distinct cultivar. These observations, measurements and descriptions were taken for 'Jazz' plants grown under the following greenhouse conditions in Assendelft, The Netherlands. The minimum day and night temperatures were 20° and 18° C., respectively. The ventilation temperature was 24° C., and the maximum light intensity was 18000 Lux. Fertilizer concentration was 0.5 to 1 EC comprising N:P:K in the ratio of 1:0.25 to 0.5:2 to 3. In addition, 3% of the total amount of fertilizer was $MgSO_4$ (15% MgO).

Frequency of fertilization varied depending on time of year and ranged from once per week to once per month. Fertilization was more frequent during the spring and summer months. Following fertilization, the plants were rinsed with sufficient clean water to remove residual fertilizer from the leaves. If fertilization frequency, or the concentration of fertilizer, is increased, 'Jazz' leaves are darker in color, eventually resulting in burning of leaves and roots. If fertilization frequency, or the concentration of fertilizer, is decreased, 'Jazz' leaves are lighter in color. If the ratio of N:K is increased above the value given above, 'Jazz' leaves become darker in color, longer and more narrow. If the ratio of N:K is decreased below the value given above, 'Jazz' leaves become lighter in color, shorter and broader. The intensity of the color of the inflorescence depends also on the amount of P.

With regard to induction of flowering, acetylene gas is allowed to bubble through 100 L of cool water for 30 min. at a pressure of 0.5 bar. Whole plants are then sprayed with the acetylene solution, making certain that the cup (vase) is filled. Spraying is done in the morning because the plants need light after this treatment, and the plants are not watered again for at least two days. The plants are treated again, following this same protocol, one week later. The plants should not be fertilized for two to three weeks following treatment with acetylene because it is likely the flowers will not form and the bracts will remain green. The description of the new cultivar 'Jazz' reported herein is based on measurements and observations of plants grown from seeds.

The following traits have been repeatedly observed to be characteristics which, in combination, distinguish Guzmania 'Jazz' from the closest comparison cultivar, Guzmania 'Jive' (U.S. Plant Pat. No. 10,968). The most important difference is the color brightness of the inflorescence. The inflorescence of Guzmania 'Jazz' is RHS 14A while that of Guzmania 'Jive' is RHS 17A.

PLANT:
Form: Funnel-form rosette.
Height: Approximately 42 cm high, when flowering.
Growth Habit: Stemless.
Diameter: Approximately 50 cm.
FOLIAGE:
Color:
  Upper surface: RHS 147A.
  Under surface: RHS 137A.
  (The color of the leaves can change depending on environmental conditions)
Size of Leaf:
  Length: Approximately 30–42 cm.
  Width: Approximately 3.0–3.5 cm.
Shape of Leaf: Linear-lanceolate.
Surface Texture: Smooth.
Orientation: Leaf blades arch continuously from the base.
Variegation: None.
BRACTS:
Length:
  Scape bracts: The lowest are approximately 30 cm long. The scape bracts just below the primary bracts are approximately 14 cm long.
  Primary bracts: The lowest are approximately 14 cm long. The bracts progress upwardly, they become shorter, with the top primary bracts being approximately 6 cm in length.

Width:
  Scape bracts: Approximately 3.5 cm.
  Primary bracts: Approximately 3.0 cm.
Number:
  Scape bracts: Approximately 10.
  Primary bracts: Approximately 12.
General Shape: Lanceolate.
Texture: Smooth.
Margin: Entire.
Color:
  Primary bracts: RHS 44B.
  Top primary bracts: RHS 14B.
FLOWERS:
Borne (stalks): Erect.
Shape of inflorescence: Compound.
Size of inflorescence on stalk: Approximately 15 cm high and approximately 20 cm in diameter.
Individual petals: (Mostly disposed within the floral bracts hidden behind the primary bracts)
  Length: Approximately 6 cm.
  Width: Approximately 0.5 cm.
  Quantity: Approximately 75 flowers divided over approximately 11 branches depending on the size of the plant.
  Color: Yellow (RHS 14A).
  Time of Blooming: A fully grown plant can bloom the whole year starting approximately eleven (11) weeks after natural induction or through treatment with acetylene.
  Duration of blooms: Each flower blooms one (1) day and the total of blooming is approximately five (5) weeks.
REPRODUCTIVE ORGANS:
  Ovaries: Superior.
  Stamens: Six (6) in number.
SEED CHARACTERISTICS: Sterile hybrid, therefore, no seed or fruit produced.

We claim:

1. A seed having American Type Culture Collection Deposit Accession No. PTA-3264 produced by crossing a Guzmania selection identified by Code No. 94206011 with a Guzmania selection identified by Code No. 94206206, said seed producing a plant that is particularly characterized by the following:
   (a) solid growth habit in a funnel-form rosette measuring approximately 42 cm in height above the pot when flowering;
   (b) numerous, relatively narrow leaves, each approximately 3–3.5 cm in width and 30–42 cm in length;
   (c) superior floral bract production;
   (d) compound inflorescence;
   (e) floral bracts are bright orange; and
   (f) long-lasting habit.

2. A plant produced from said seed according to claim 1 and accorded American Type Culture Collection Deposit Accession No. PTA-3264.

3. The pollen produced by the plant according to claim 2.

4. The inflorescence produced by the plant according to claim 2.

5. A method of producing Guzmania progeny plant comprising the steps of (a) crossing Guzmania cultivar 'Jazz' produced from seed accorded American Type Culture Collection Deposit Accession No. PTA-3264 with another Guzmania plant and (b) selecting progeny.

* * * * *